US010143712B2

(12) United States Patent
Nikawa

(10) Patent No.: US 10,143,712 B2
(45) Date of Patent: Dec. 4, 2018

(54) PROPHYLACTIC, AMELIORATING OR THERAPEUTIC AGENT FOR ORAL DISEASES

(71) Applicant: HIROSHIMA UNIVERSITY, Higashi-Hiroshima-shi (JP)

(72) Inventor: Hiroki Nikawa, Hiroshima (JP)

(73) Assignee: HIROSHIMA UNIVERSITY, Higashi-Hiroshima-shi (JP)

( * ) Notice: Subject to any disclaimer, the term of this patent is extended or adjusted under 35 U.S.C. 154(b) by 81 days.

(21) Appl. No.: 14/745,557

(22) Filed: Jun. 22, 2015

(65) Prior Publication Data

US 2016/0101136 A1 Apr. 14, 2016

Related U.S. Application Data

(62) Division of application No. 13/382,087, filed as application No. PCT/JP2010/004626 on Jul. 16, 2010, now abandoned.

(30) Foreign Application Priority Data

Jul. 16, 2009 (JP) .................. 2009-168122

(51) Int. Cl.
  *A23C 9/123* (2006.01)
  *A61K 35/747* (2015.01)

(52) U.S. Cl.
  CPC ............ *A61K 35/747* (2013.01); *A23C 9/123* (2013.01); *A23Y 2220/73* (2013.01)

(58) Field of Classification Search
  None
  See application file for complete search history.

(56) References Cited

U.S. PATENT DOCUMENTS

| 6,479,051 B1 | 11/2002 | Bruce et al. |
| 8,192,978 B2 | 6/2012 | Kaesler et al. |
| 2003/0157079 A1 | 8/2003 | Kato et al. |
| 2004/0146493 A1 | 7/2004 | Mollstam et al. |
| 2005/0002874 A1 | 1/2005 | Mollstam et al. |
| 2005/0129629 A1 | 6/2005 | Mollstam et al. |
| 2005/0158254 A1 | 7/2005 | Mollstam et al. |
| 2005/0281756 A1 | 12/2005 | Connolly et al. |
| 2007/0071737 A1 | 3/2007 | Koga |
| 2008/0118444 A1 | 5/2008 | Hsu et al. |
| 2009/0123394 A1 | 5/2009 | Mollstam et al. |
| 2009/0238774 A1 | 9/2009 | Connolly et al. |

FOREIGN PATENT DOCUMENTS

| JP | 2003 299480 | 10/2003 |
| JP | 2008 502360 | 1/2008 |
| JP | 2008 37859 | 2/2008 |
| JP | 2008 237198 | 10/2008 |
| JP | 2009-78995 A | 4/2009 |
| WO | 02 16554 | 2/2002 |
| WO | 03 082027 | 10/2003 |

OTHER PUBLICATIONS

Nase et al., Caries Res 2001;35:412-420.*
Hiyama, A, et al., "Action of Lactic Acid Bacterium Strain Derived From Oral Cavity to Inhibit Mutans Strepococci and Candida," Hiroshime Daigaku Shigaku Zasshi, vol. 41, No. 1, pp. 93-94, (Jun. 2009) (with English translation).
Mimura, S., et al. "Inhibitory effect of oral isolates of *Lactobacillus* spp. on mutans strepococci," Journal of Nippon Academy of Dental Technology, vol. 29, p. 238, (2008) (with English abstract).
International Search Report dated Sep. 7, 2010 in PCT/JP10/04626 Filed Jul. 16, 2010.
Koll-Klais et al., Oral Microbiology Immunology 2005: 20: 354-361.
Extended European Search Report dated Feb. 7, 2013 in Patent Application No. 10799648.0.
P. Kõll-Klais, et al., "Oral lactobacilli in chronic periodontitis and periodontal health: species composition and antimicrobial activity", Oral Microbiology and Immunology, Munksgaard, Copenhagen, DK, ISSN: 0902-0055, DOI: 10.1111/J.1399-302X.2005.00239.X, XP009166559A, vol. 20, No. 6, Dec. 1, 2005, pp. 354-361.
S. I. Smith, et al., "Lactobacilli in human dental caries and saliva", Microbios, Cambridge, GB, ISSN: 0026-2633, XP009138831A, vol. 105, No. 411, Jan. 1, 2001, pp. 77-85.
Combined Office Action and Search Report dated Jan. 25, 2013 in Chinese Patent Application No. 201080031871.X with English translation of categories of cited documents.

(Continued)

*Primary Examiner* — Irene Marx
(74) *Attorney, Agent, or Firm* — Oblon, McClelland, Maier & Neustadt, L.L.P.

(57) ABSTRACT

To provide a novel lactic acid bacterium strain having a broad antibacterial spectrum against bacteria that cause oral diseases, from which a fermented product having good flavor and being excellent in palatability can be produced, and a prophylactic, ameliorating or therapeutic agent for oral diseases using the same.

A prophylactic, ameliorating or therapeutic agent for an oral disease, which contains a lactic acid bacterial cell of one or more kinds selected from the group consisting of *Lactobacillus rhamnosus* strain KO3, *Lactobacillus casei* strain YU3 and *Lactobacillus paracasei* strain YU4 or a culture of the cell, or an extract thereof, as an active ingredient.

10 Claims, 10 Drawing Sheets

(56) References Cited

OTHER PUBLICATIONS

Min Zhu, et al., "Detection of the Acid-resistant Gene ffh in Lactobacillus Casei and Its cloning", Journal of Oral Science Research, vol. 20, No. 4, Aug. 31, 2004, pp. 395-397 with English abstract.

Dong-mei Liu, et al. "Study on inhibitory effect and characterisation of antimicrobial substances produced by Lactobacillus rhamnosus", Diary Industry, vol. 34, No. 1, Dec. 31, 2006, pp. 13-16 with English abstract.

* cited by examiner

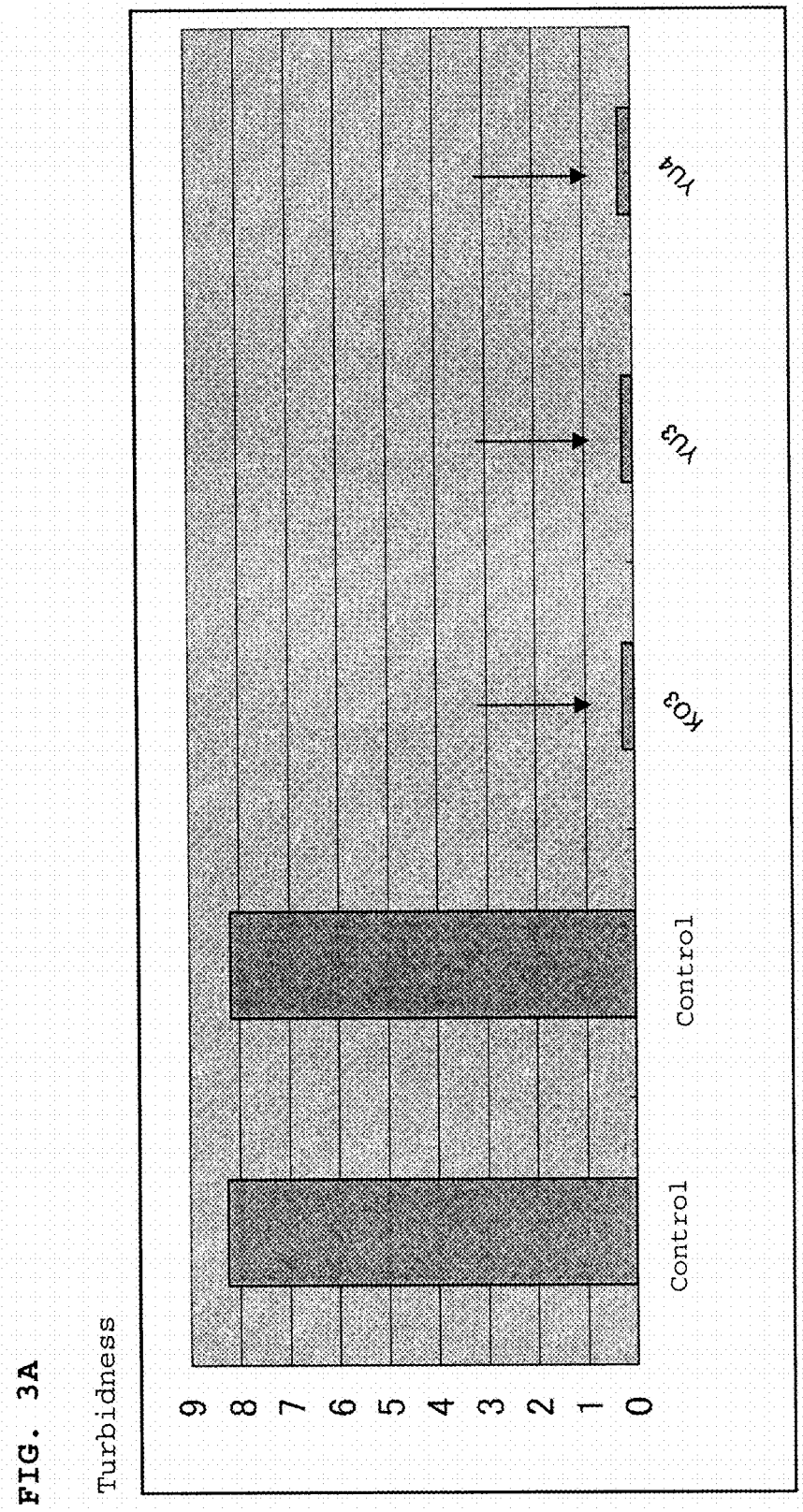

Amount of ATP (pmol/sample)

Amount of ATP (pmol/well)

Amount of ATP (pmol/well)

PROPHYLACTIC, AMELIORATING OR THERAPEUTIC AGENT FOR ORAL DISEASES

This application is a divisional of U.S. application Ser. No. 13/382,087 filed Jan. 3, 2012, pending, which is a National Stage of PCT/JP10/004626 filed Jul. 16, 2010 and claims the benefit of JP 2009-168122 filed Jul. 16, 2009.

FIELD OF THE INVENTION

The present invention relates to a prophylactic, ameliorating or therapeutic agent for oral diseases such as dental caries or periodontal diseases.

BACKGROUND OF THE INVENTION

A bacterial flora in the oral cavity is constituted by 400 to 500 kinds of microorganisms. Therefore, various pathogenic microorganisms such as cariogenic bacteria, periodontal disease bacteria and *candida* bacteria are present in the oral cavity, which causes various diseases such as dental caries, periodontal diseases, glossitis, thrush and oral candidiasis. Furthermore, it is reported in recent studies that *candida* bacteria also relate to periodontal diseases.

Therefore, many suggestions have been heretofore made with respect to oral compositions containing an antibacterial substance. However, even an antibacterial agent was administered to the oral cavity, the antibacterial agent was washed out by saliva or a food or beverage within a short time, and thus the effect thereof had to be said to be a transient effect.

Furthermore, in view of that a lactic acid bacterium suppresses bacteria causing various diseases in the large intestine, studies for applying the technique thereof to dental diseases have been done. For example, it was reported that lactic acid bacteria such as *Lactobacillus salivarius* (Patent Document 1 and Patent Document 2), *Lactobacillus reuteri* (Patent Document 3 and Patent Document 4), *Lactobacillus paracasei* (Patent Document 5), *Lactobacillus delbrueckii* (Patent Document 6) and *Lactobacillus fermentum* (Non-patent Document 1) are effective for the prophylaxis of dental caries and periodontal diseases.

However, there was also a problem that even a lactic acid bacterium having an antibacterial effect against cariogenic bacteria and periodontal disease bacteria has a narrow antibacterial spectrum, has insufficient fermentability and thus cannot provide a good fermented product, and cannot provide a fermented product having good flavor and being excellent in palatability.

PRIOR ART DOCUMENTS

Patent Document

Patent Document 1: WO 2002/016554
Patent Document 2: WO 2003/082027
Patent Document 3: Japanese Patent Application Laid-Open (JP-A) No. 2003-299480
Patent Document 4: Japanese Patent Application National Publication (Laid-Open) No. 2008-502360
Patent Document 5: JP-A-2008-37859
Patent Document 6: JP-A-2008-237198

Non-Patent Documents

Non-patent Document 1: Sumiyo MIMURA, Hiroki NIKAWA, Seicho MAKIHIRA, and Aya HIYAMA, the Journal of Nippon Academy of Dental Technology, Vol. 29, special issue, 238 (2008)

SUMMARY OF THE INVENTION

Problem to be Solved by the Invention

The present invention relates to provision of a novel lactic acid bacterium strain, having a broad antibacterial spectrum against bacteria that cause oral diseases, from which a fermented product having good flavor and being excellent in palatability can be produced, and to provision of a food and a prophylactic, ameliorating or therapeutic agent for oral diseases containing the same.

Means for Solving the Problem

The present inventors have done intensive studies on oral microorganisms, and found that specific lactic acid bacterium strains belonging to *Lactobacillus* rhamnosus, *Lactobacillus* casei and *Lactobacillus paracasei* that are present in saliva have an excellent antibacterial effect against any of cariogenic bacteria, periodontal disease bacteria and *candida* bacteria, and that a fermented product being excellent in palatability can be produced by using these.

Therefore, the present invention relates to the following 1) to 8).

1) A prophylactic, ameliorating or therapeutic agent for an oral disease, which contains a lactic acid bacterial cell of one or more kinds selected from the group consisting of *Lactobacillus* rhamnosus strain KO3 (NITE BP-771), *Lactobacillus casei* strain YU3 (NITE BP-772) and *Lactobacillus paracasei* strain YU4 (NITE BP-775) or a culture of the cells, or an extract thereof, as an active ingredient.

2) A food containing a lactic acid bacterial cell of one or more kinds selected from the group consisting of *Lactobacillus* rhamnosus strain KO3 (NITE BP-771), *Lactobacillus casei* strain YU3 (NITE BP-772) and *Lactobacillus paracasei* strain YU4 (NITE BP-775) or a culture of the cell, or an extract thereof.

3) The food according to the above-mentioned 2), which is a fermented milk or a fermented beverage.

4) An agent for the suppression of the proliferation of a cariogenic bacterium, a periodontal disease bacterium and a *candida* bacterium, which contains a lactic acid bacterial cell of one or more kinds selected from the group consisting of *Lactobacillus* rhamnosus strain KO3 (NITE BP-771), *Lactobacillus casei* strain YU3 (NITE BP-772) and *Lactobacillus paracasei* strain YU4 (NITE BP-775) or a culture of the cell, or an extract thereof, as an active ingredient.

5) The agent for the suppression of the proliferation of a cariogenic bacterium, a periodontal disease bacterium and a *candida* bacterium according to 4), wherein the cariogenic bacterium, periodontal disease bacterium and *candida* bacterium are at least *Streptococcus mutans*, *Streptococcus sobrinus*, *Porphyromonas gingivalis* and *Candida albicans*.

6) *Lactobacillus* rhamnosus strain KO3 that has been deposited as NITE BP-771, *Lactobacillus casei* strain YU3 that has been deposited as NITE BP-772 and *Lactobacillus paracasei* strain YU4 that was deposited as NITE BP-775, at the Patent Microorganisms Depositary of the National Institute of Technology and Evaluation.

7) A lactic acid bacterial cell of one or more kinds selected from the group consisting of *Lactobacillus* rhamnosus strain KO3 (NITE BP-771), *Lactobacillus casei* strain YU3 (NITE BP-772) and *Lactobacillus paracasei* strain YU4 (NITE BP-775) or a culture of the cell, or an extract thereof, which is used as a prophylactic, ameliorating or therapeutic agent for an oral disease.

8) A method for the prophylaxis, amelioration or treatment of an oral disease, which includes administering or ingesting a lactic acid bacterial cell of one or more kinds selected from the group consisting of Lactobacillus rhamnosus strain KO3 (NITE BP-771), Lactobacillus casei strain YU3 (NITE BP-772) and Lactobacillus paracasei strain YU4 (NITE BP-775) or a culture of the cell, or an extract thereof.

Effects of the Invention

According to the present invention, a food with high palatability, a medicament, an oral composition and the like, which exert a prophylactic, ameliorating or therapeutic effect for various oral diseases such as dental caries, periodontal diseases, glossitis, thrush and oral candidiasis.

BRIEF DESCRIPTION OF THE DRAWINGS

FIG. 3A is a graph showing the growth-inhibiting effect against Porphyromonas gingivalis.

FIG. 8A shows a graph of cariogenic bacteria and FIG. 8B shows a graph of P. intermedia (Pi).

FIG. 8C shows a graph of T. forsythensis (Tf) and FIG. 8D shows a graph of F. nucleatum (Fuso).

MODES FOR CARRYING OUT THE INVENTION

Figure 1A:
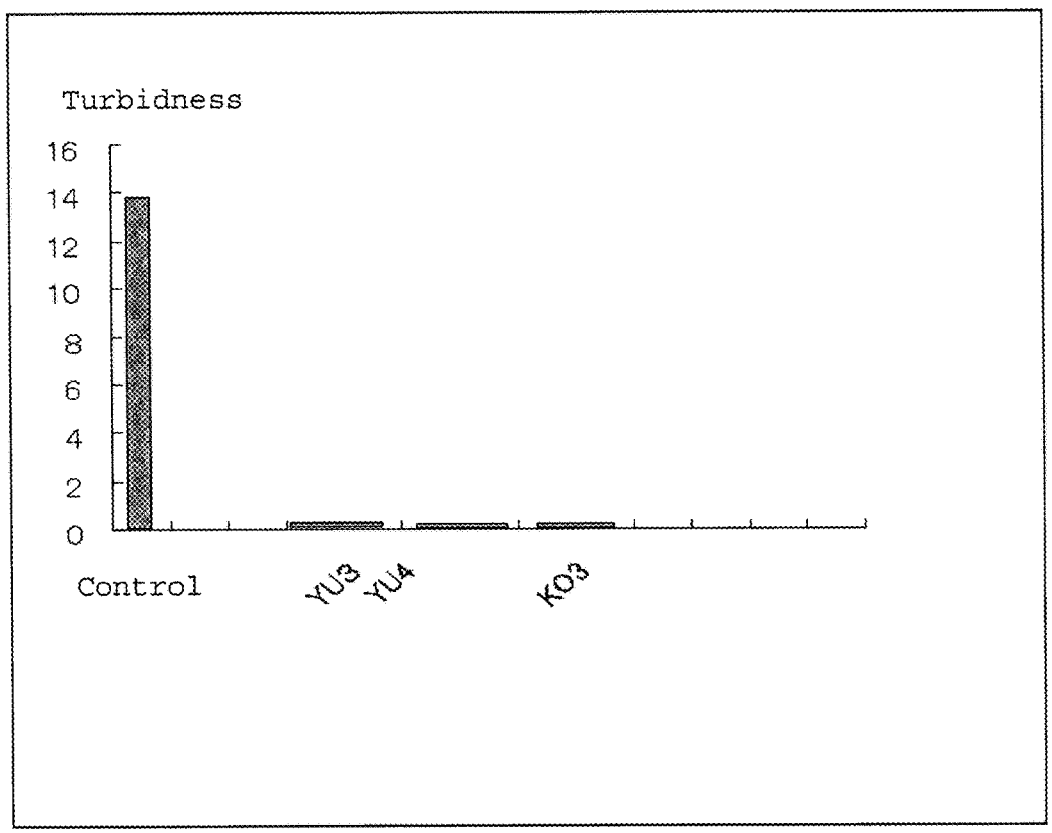
FIG. 1A is a graph showing the growth-inhibiting effect against Streptococcus mutans.
Figure 1B:
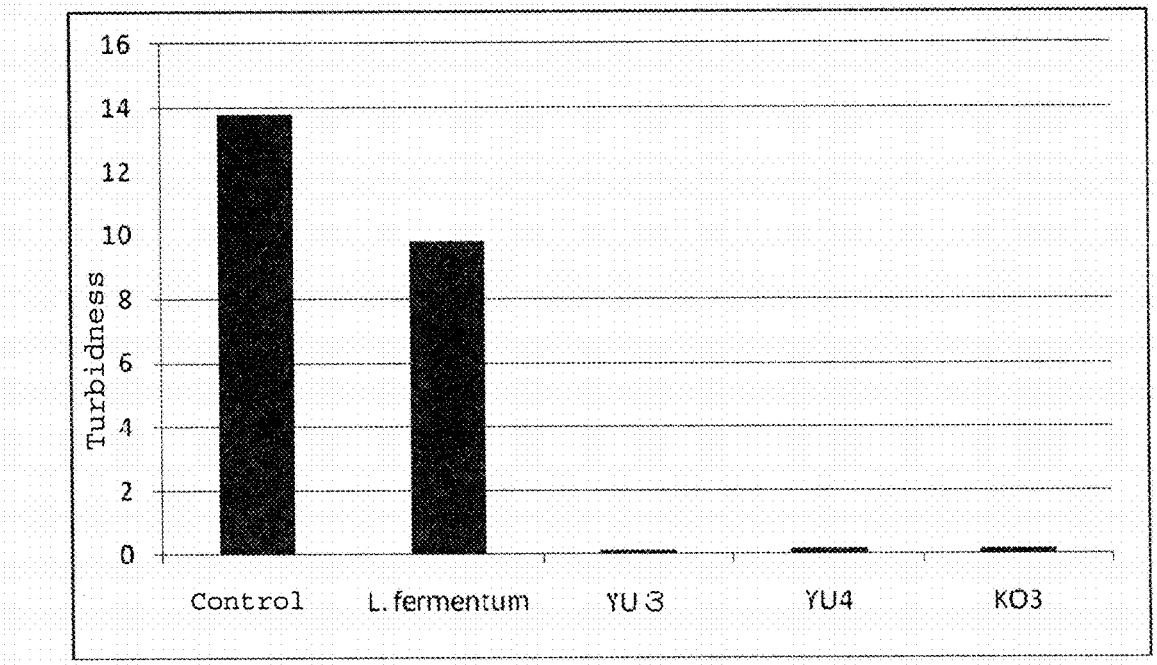
FIG. 1B is a graph showing the growth-inhibiting effect against Streptococcus mutans.
Figure 2:
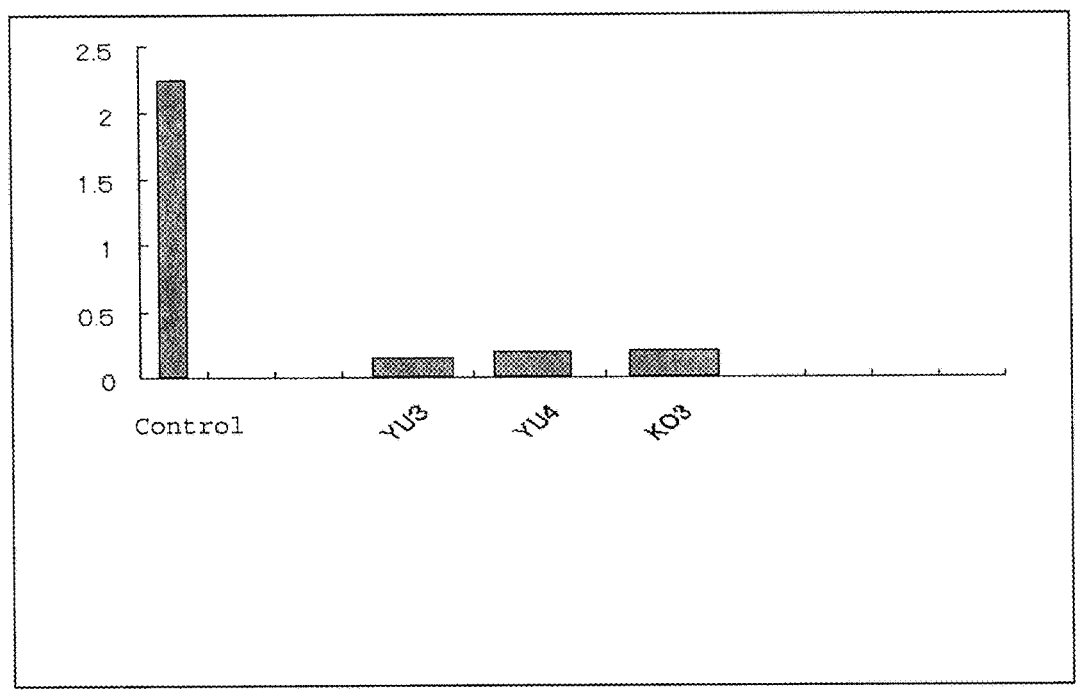
FIG. 2 is a graph showing the growth-inhibiting effect against Streptococcus sobrinus.
Figure 3B:
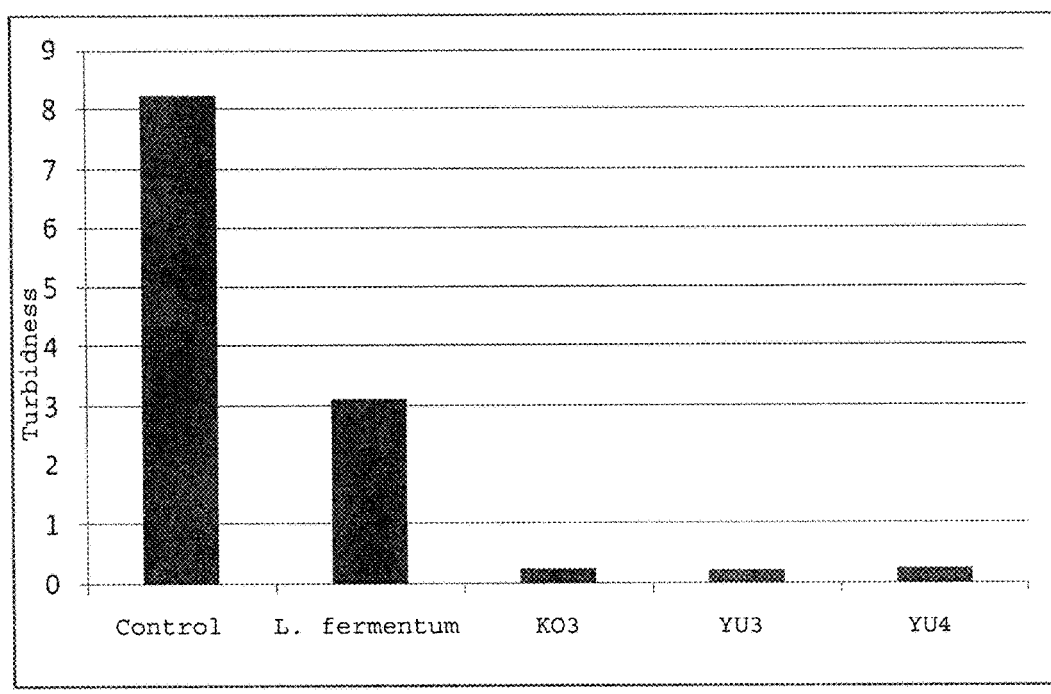
FIG. 3B is a graph showing the growth-inhibiting effect against Porphyromonas gingivalis.
Figure 4A:
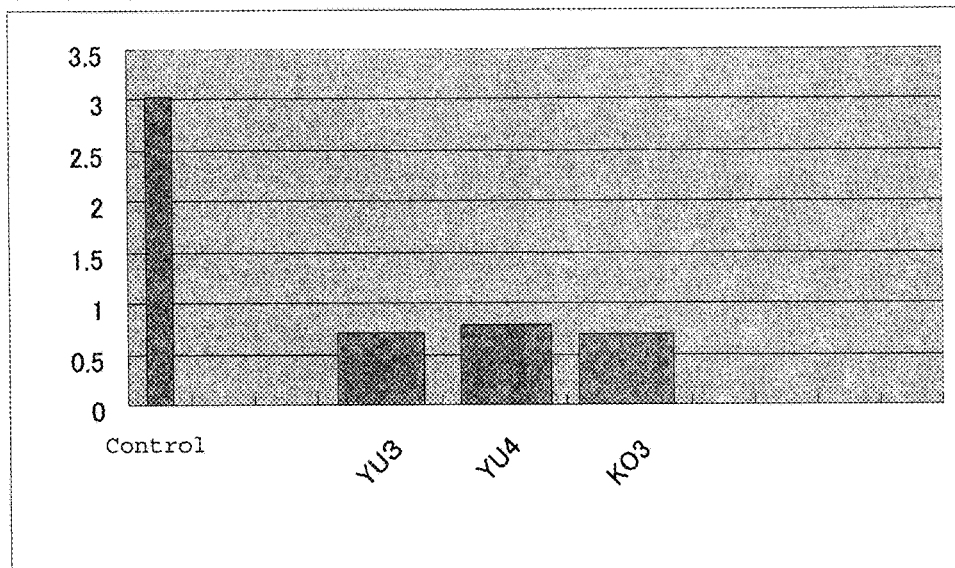
FIG. 4A is a graph showing the growth-inhibiting effect against Candida albicans.
Figure 4B:
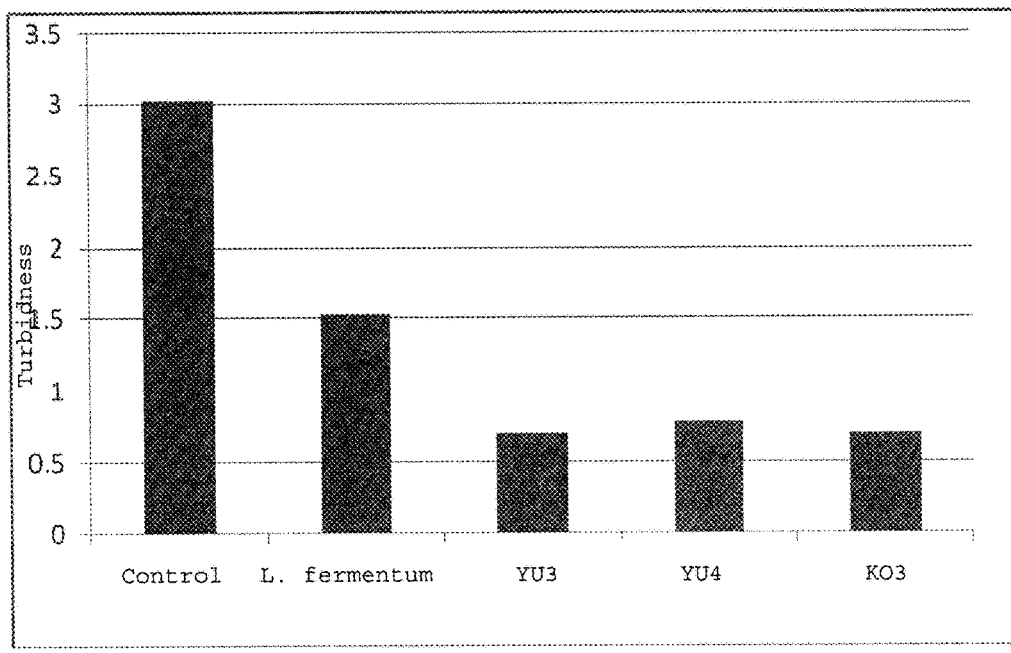
FIG. 4B is a graph showing the growth-inhibiting effect against Candida albicans.

The lactic acid bacteria used for the fermented milk of the present invention are lactic acid bacteria belonging to Lactobacillus rhamnosus, Lactobacillus casei and Lactobacillus paracasei; specifically, they are Lactobacillus rhamnosus strain KO3 that was deposited as NITE BP-771 on Jun. 10, 2009, Lactobacillus casei strain YU3 that has been deposited as NITE BP-772 on Jun. 10, 2009, and Lactobacillus paracasei strain YU4 that has been deposited as NITE BP-775 on Jun. 24, 2009, at the Patent Microorganisms Depositary of the National Institute of Technology and Evaluation (Address: 2-5-8 Kazusakamatari, Kisarazu-shi, Chiba 292-0818, Japan).

The KO3 strain was first separated from human saliva by the present inventors, and was identified as Lactobacillus rhamnosus since the base sequence of 16S rRNA shows a homology of 100% with the base sequence of Lactobacillus rhamnosus strain IDCC3201 between 1485/1485, and bears the aspect of a cram-positive bacillus under a microscope after gram staining. The major mycological properties of the KO3 strain are shown below.

1) Gram-positive lactobacillus, 2) homo-type lactic fermentation, 3) catalase negative, 4) no endospore formability, 5) culturable under aerobic conditions, and 6) producing exopolysaccharide.

The YU3 strain was first separated from human saliva by the present inventors, and was identified as Lactobacillus casei since the base sequence of 16S rRNA shows a homology of 100% with the base sequence of Lactobacillus casei ATCC 334 between 1485/1485, and bears the aspect of a cram-positive bacillus under a microscope after gram staining. The major mycological properties of the YU3 strain are shown below.

1) Gram-positive lactococcus, 2) homo-type lactic fermentation, 3) catalase negative, 4) no endospore formability, 5) culturable under aerobic conditions, and 6) producing exopolysaccharide.

The YU4 strain was first separated from human saliva by the present inventors, and was identified as Lactobacillus paracasei since the base sequence of 16S rRNA shows a homology of 1477/1477 (100%) with the Partial Sequence of Lactobacillus paracasei strain DJ1 16S ribosomal RNA gene, and bears the aspect of a gram-positive bacillus under a microscope after gram staining. The major mycological properties of the YU4 strain are shown below.

1) Gram-positive lactococcus, 2) homo-type lactic fermentation, 3) catalase negative, 4) no endospore formability, 5) culturable under aerobic conditions, and 6) producing exopolysaccharide.

In the present invention, the above-mentioned lactic acid bacterial cell that has been recovered by culturing the bacterium according to a general method for culturing a lactic acid bacterium and has been separated from the culture by cell-collecting means such as centrifugation may be used directly. Alternatively, the cultured and fermented liquid (culture supernatant), a concentrated liquid thereof, or a cytoplasma or cell wall fraction obtained by treating the bacterial cell through an enzyme or a physical means may also be used. Furthermore, not only a viable cell but also a killed cell may be used.

The medium for culturing the lactic acid bacterium used in the present invention includes various media such as a fruit juice medium, a vegetable juice medium, a milk medium, a skimmed milk medium or a medium containing a milk component, and a semi-synthetic medium free of a milk component. Examples of such the medium may include a reduced skimmed milk medium produced through heat-sterilized skimmed milk, a skimmed milk medium to which yeast extract has been added, an MRS medium, and a GAM medium.

No particular limitation imposed on the culturing method, so long as the method allows favorable growth of the target cells. Examples of the method include stationary culture, neutralization culture (as a constant pH), batch culture and continuous culture.

The extract of lactic acid bacterial cell or the culture of the cell of the present invention means various solvent extract liquids obtained by extracting the cell or the culture of the cell with a solvent, a diluted liquid thereof, a concentrated liquid thereof or a dried powder thereof.

As the extraction solvent used for obtaining the extract of the present invention, either a polar solvent or nonpolar solvent can be used, or these can be used after mixing. Examples may include water; alcohols such as methanol, ethanol, propanol and butanol; polyols such as propylene glycol and butylene glycol; ketones such as acetone and methyl ethyl ketone; esters such as methyl acetate and ethyl acetate; chain and cyclic ethers such as tetrahydrofuran and diethyl ether; polyethers such as polyethylene glycol; hydrocarbons such as hexane, cyclohexane and petroleum ethers; aromatic hydrocarbons such as benzene and toluene; pyridines, and the like, and among these, esters such as ethyl acetate and alcohols such as ethanol are preferable.

Although the conditions for extraction differ depending on the solvent to be used, it is preferable to conduct extraction, for example, by using from 1 to 10 parts by mass of a solvent with respect to 1 part by mass of a culture liquid at a temperature of from 0 to 50° C., preferably of from 25 to 37° C., for from 0.5 hour to 3 hours.

The above-mentioned extract may be used as is, or may be used after diluting, concentrating or lyophilizing the extract and thereafter forming the product into a powder or paste if necessary. Alternatively, the extract may also be used after appropriate purification by a purification technique such as liquid-liquid distribution.

The "oral disease" in the prophylactic, ameliorating or therapeutic agent for an oral disease of the present invention refers to oral diseases that are caused by cariogenic bacteria, periodontal disease bacteria and *candida* bacteria, and examples may include dental caries; periodontal diseases such as gingivitis and periodontitis, oral candidiasis such as glossitis, thrush and angular stomatitis, and the like.

Examples of the cariogenic bacteria may include *Streptococcus mutans* and *Streptococcus sobrinus*; examples of the periodontal disease bacteria may include *Porphyromonas gingivalis, Prevotella intermedia, Treponema denticola, Tannerella forsythensis, Actinobacillus actinomycetemcomitans, Fusobacterium nucleatum* and the like; and examples of the *candida* bacteria may include *Candida albicans, Candida glabrata, Candida tropicalis* and the like.

As shown in the following Examples, the lactic acid bacterium of the present invention has a growth suppressing effect against any of *Streptococcus mutans* and *Streptococcus sobrinus* that are cariogenic bacteria, *Porphyromonas gingivalis* that is a periodontal disease bacterium, and *Candida albicans* that is a *candida* bacterium. Furthermore, it has an effect of suppressing the proliferation of *Fusobacterium* bacteria such as *Fusobacterium. nucleatum* that is known as a subgingival plaque former in the oral cavity. Furthermore, a fermented milk prepared by using the lactic acid bacterium has good flavor and texture, and even it is present together with other lactic acid bacterium in an existing fermented milk such as *Lactobacillus. bulgaricus*, the taste thereof is not impaired or can further be improved.

Therefore, the lactic acid bacterial cell or the culture of the cell, or the extract thereof can be a prophylactic, ameliorating or therapeutic agent for oral diseases, or an agent for suppressing the proliferation of cariogenic bacteria, periodontal disease bacteria and *candida* bacteria. Such prophylactic, ameliorating or therapeutic agent for oral diseases and agent for suppressing the proliferation of cariogenic bacteria, periodontal disease bacteria and *candida* bacteria can be used as they are, as foods, medicaments, oral compositions and the like, for the prophylaxis, amelioration or treatment of oral diseases such as dental caries, periodontal diseases and oral candidiasis that are caused by pathogenic microorganisms in the oral cavity, or for the suppression of the proliferation of cariogenic bacteria, periodontal disease bacteria and *candida* bacteria, and can also be used as materials for incorporating in foods, medicaments or oral compositions. Furthermore, the foods can also be health foods, supplements or functional foods such as foods for specified health use, and have a product concept of the prophylaxis, amelioration or the like of tooth decay, periodontal diseases and other oral infectious diseases and include a label indicating such effects as necessary.

The form in the case when used as a medicament is preferably a form of oral administration, and the dosage form thereof may include various forms such as liquid agents; solid agents such as pills, granules, fine granules, powders and tablets; or capsules in which the liquid agent or solid agent is encapsulated, oral sprays, troches, and the like. In order to prepare pharmaceutical formulations and supplements having such various dosage forms, other excipients, binders, bulking agents, disintegrating agents, surfactants, lubricants, dispersing agents, buffer agents, preservatives, flavoring agents, fragrances, coating agents, carriers, diluents and the like that are pharmaceutically acceptable can be used in suitable combination to the extent that the actions of the cell and culture of the present invention are not obstructed.

The content of the lactic acid bacterial cell or the culture of the cell, or the extract thereof of the present invention in the oral pharmaceutical formulation when it is used as such formulation is from 1% by mass to 50% by mass, preferably from 10% by mass to 20% by mass in the whole composition.

Examples of the form in the case of use as a food may include beverages such as fruit juice or vegetable juice beverages, carbonated beverages, tea-based beverages, milk beverages, fermented milks, fermented fruit juices, fermented vegetable juices, alcoholic beverages and soft drinks; various foods such as jelly-like foods, various snacks, baked confectioneries, cakes, chocolates, jams, breads, gums, candies, soups, pickles and foods boiled in soy; supplements having the same forms as those for the above-mentioned oral pharmaceutical formulation (pills, capsules, syrups and the like); and the like.

The culture of the lactic acid bacterium of the present invention becomes a fermented food such as yogurts, cheeses, miso, soybean sauces and pickles, and such fermented milks or cheeses can be used as a material to form breads, snacks, cakes and the like for the prophylaxis or amelioration of tooth decay and periodontal diseases.

The fermentation by utilizing the lactic acid bacterium of the present invention is preferably a method including preparing a starter in advance, and fermenting by inoculating the starter to a raw material substance for fermentation. Typical examples of the starter may include those obtained by inoculating a lactic acid bacterium into a raw material substance for fermentation that has been subjected to a general sterilization treatment in advance, such as a 10%, powdered skimmed milk to which a yeast extract has been added, and conducting culturing. In addition, if necessary, a substance for promoting fermentation such as carbon sources such as glucose, starch, sucrose, lactose, dextrin, sorbitol and fructose; nitrogen sources such as yeast extract and peptone; vitamins; minerals; and the like can be added to the raw material substance for fermentation.

It is adequate that the amount of inoculation of a lactic acid bacterium is generally selected from an amount by which cell is included in amount of about $1\times10^6$ cells or more, preferably around $1\times10^7$ cells, in 1 mL of a liquid containing the raw material substance for fermentation. The culturing conditions are generally selected from a fermentation temperature of from about 20 to 42° C., preferably from about 25 to 37° C., and a fermentation time of from about 5 to 72 hours. The thus-obtained lactic acid fermented product has a card-like form (yogurt-like form), and the product can directly become a solid food. The lactic acid fermented product having a card-like form can be formed into a desired beverage form by further homogenizing it.

Examples of the specific form in the case when the prophylactic, ameliorating, therapeutic agent for oral diseases, or the like of the present invention is used as an oral composition may include mouth rinses, mouthwashes, toothpastes, tooth powders, tooth liquids, oral ointments, gel agents, pills, granules, fine granules, gummy jellies, troches, tablets, capsules, candies, chewing gums and the like, and preferable examples may include toothpastes, mouth rinses, gummy jellies and troches.

The content of the lactic acid bacterium of the present invention in the above-mentioned medicament or food is not specifically limited and may be suitably adjusted depending on a daily dose and the like; for example, when the dosage form is a liquid, the concentration of the lactic acid bacterial cell is preferably from $1\times10^6$ cells/ml to $1\times10^8$ cells/ml, and when the dosage form is a solid, the concentration is preferably from $1\times10^7$ cells/g to $1\times10^{10}$ cells/g.

When the lactic acid bacterium of the present invention is administered as a viable cell, it is preferably administered by from $1\times10^8$ to $5\times10^{10}$ cfu/day per an adult human.

Hereinafter the present invention will be explained in more detail with referring to the Examples and Test Examples.

EXAMPLES

Preparation Example 1 Preparation of Lactic Acid Bacterial Cells

An MRS medium (Difco) is sterilized at 121° C. for 20 minutes, and *Lactobacillus rhamnosus* strain KO3 (this was deposited as NITE BP-771 with the Patent Microorganisms Depositary of the National Institute of Technology and Evaluation (Address: 2-5-8 Kazusakamatari, Kisarazu-shi, Chiba 292-0818, Japan) (Jun. 10, 2009)) is inoculated, cultured at 37° C. for 48 hours in the air and washed with distilled water, ultrapure water, a buffer liquid or the like, thereby a cell can be obtained.

Similarly, an MRS medium (Difco) is sterilized at 121° C. for 20 minutes, and *Lactobacillus casei* strain YU3 (this was deposited as NITE BP-772 with the Patent Microorganisms Depositary of the National Institute of Technology and Evaluation (Address: 2-5-8 Kazusakamatari, Kisarazu-shi, Chiba 292-0818, Japan) (Jun. 10, 2009)) is inoculated, cultured at 37° C. for 48 hours in the air and washed with distilled water, ultrapure water, a buffer liquid or the like, thereby a cell can be obtained.

Furthermore, an MRS medium (Difco) is sterilized at 121° C. for 20 minutes, and *Lactobacillus paracasei* strain YU4 (this was deposited as NITE BP-775 with the Patent Microorganisms Depositary of the National Institute of Technology and Evaluation (Address: 2-5-8 Kazusakamatari, Kisarazu-shi, Chiba 292-0818, Japan) (Jun. 24, 2009)) is inoculated, cultured at 37° C. for 48 hours in the air and washed with distilled water, ultrapure water, a buffer liquid or the like, thereby a cell can be obtained.

In addition, *Lactobacillus Fermentum* used for comparison was cultured in a similar manner to that mentioned above by using *Lactobacillus Fermentum* strain SU3 collected from the human oral cavity described in the above-mentioned Non-patent Document 1, and subjected to the tests.

Test Example 1 Antibacterial Actions Against Cariogenic Bacteria, Periodontal Disease Bacteria and *Candida* Bacteria Test Method Each cell that had been stored at −80° C. was thawed at an ordinary temperature, collected by centrifugation (3000 rpm for 5 min), and washed twice by sterilized distilled water (MQ water) to adjust to 0.3 at OD600 (about $1.0\times10^8$ cfu/ml). 500 µl of each suspension liquid was inoculated into 15 ml of MRS Broth or Brain Heart Infusion Broth (hereinafter referred to as BHI Broth: Difco), and stationary culture was conducted at 37° C. for 48 hours. Thereafter centrifugation was conducted at 3000 rpm for 5 minutes (room temperature), and the supernatant was collected and used for an antibacterial assay.

<Test Strains>

*Streptococcus mutans* Ingbritt and *Streptococcus sobrinus* B13 were used as cariogenic bacteria (*mutans* streptococci). For the preculturing of these bacteria, Tryptic Soy Broth (hereinafter referred to as TSBY: Difco) to which 5% of Yeast Extract (Difco) had been added was used, and the culturing was conducted at 37° C. for 24 hours. Thereafter the bacteria were washed twice with MQ water, adjusted to 0.3 at OD600 (*Streptococcus mutans* Ingbritt; $1.0\times10^8$ cfu/ml, *Streptococcus sobrinus* B13; $1.0\times10^8$ cfu/ml) and the thus-prepared strain was used.

*Porphyromonas gingivalis* strain 381 was used as a periodontal disease bacterium; this was precultured by using a GAM medium to which 1% hemin and 0.2% vitamin K had been added, at 37° C. for 7 days in an anaerobic jar containing AneroPack (MCG) (BBL, Cookeysville, USA) (10% $CO_2$). Thereafter the bacterium was washed twice with phosphate buffer (pH 7.4; PBS), adjusted to 0.3 at OD600 (about $0.5\times10^7$ cfu/ml) and the thus-prepared strain was used.

Furthermore, *Candida albicans* MYA274 was used as *candida*; this was precultured at 37° C. for 24 hours by using Sabouraud Dextrose Broth (Difco), washed twice with MQ water, adjusted to 0.3 at OD600 (*Candida albicans* MYA274; $1.0\times10^7$ cells/ml) and the thus-prepared strain was used.

<Antibacterial Assay>

One ml of TSBY for the cariogenic bacterium, a GAM medium or BHI medium to which 1% of hemin and 0.2% of vitamin K had been added for the periodontal disease bacterium or Sabouraud Broth for the *candida*, 1 ml of each supernatant, and 50 µl of the bacterial suspension of the lactic acid bacterium that had been adjusted to 0.3 at OD600 were inoculated into a 24-well plate, and a turbidness was measured at 37° C. in 24 hours. As a control, a control to which 50 µl of a bacterial suspension had been inoculated, wherein the bacterial suspension was obtained by adding 1 ml of a similar medium to that used in the preculture of the lactic acid bacterium, i.e., MRS Broth or BHI Broth, to 1 ml of TSBY or Sabouraud Broth and adjusting the medium to 0.3 at OD600, was used. Furthermore, four similar samples were made for each supernatant, and for the control, and an average value±SD was calculated.

The results are shown in FIGS. 1A and 1B, FIG. 2, FIGS. 3A and 3B, and FIGS. 4A and 4B.

The strains YU3, YU4 and KO3 showed a high proliferation-suppressing effect against all of *Streptococcus mutans, Streptococcus sobrinus, Porphyromonas gingivalis* and *Candida albicans*. Furthermore, the antibacterial effects thereof were superior to that of known *Lactobacillus Fermentum* strain SU3.

Test Example 2 Biofilm-Inhibiting Action

A biofilm assay by *Candida albicans* was conducted according to the method of Nikawa et al., 1996 (Nikawa, H., Nishimura, H. Yamamoto, T., Hamada, T. & Samaranayake, L. P.: The role of saliva and serum in *Candida albicans* biofilm formation on denture acrylic surfaces. Microbial Ecol Health & Dis 9, 35-48, 1996). Using a resin for a denture base (Bio Resin, Shofu, Kyoto), 50×50×0.2 mm of the resin sample was polymerized according to a general procedure at a liquid mixing ratio as instructed by the manufacturer. This was cut into 10×10×0.2 mm by using a resin cutter and used for a biofilm assay.

The resin plate was put on the bottom surface of a 24-well plate, and 500 µl of human blood serum (Type, Sigma co. human male AB plasma) was added thereto, and incubation was conducted at 37° C. for 1 hour. Thereafter the human blood serum was removed. 50 µl of a suspension liquid of *Candida albicans* strain MYA274, which had been adjusted to 0.3 at OD600, was inoculated onto the surface of the sample, and the sample was stood still at 37° C. for 2 hours to promote the fixing. Thereafter 1 ml of the MRS culture supernatant and 1 ml of Sabouraud Broth were added, and culturing was conducted at 37° C. for 72 hours. The resin sample was removed gently so that the biofilm formed on the surface of the sample was not broken, and washed with 400 ml of MQ water for 5 seconds to remove excess bacteria. The amount of the biofilm formed on the resin sample was examined by extracting ATP and quantifying the ATP by using a luminometer (AB2200 Luminescencer PSN, ATTO, Tokyo). In addition, a control to which the same amount of MRS Broth had been added instead of the culture supernatant of the lactic acid bacterium was used. Furthermore, four similar samples were made for each supernatant, and for the control, and an average value±SD was calculated.

Figure 5:
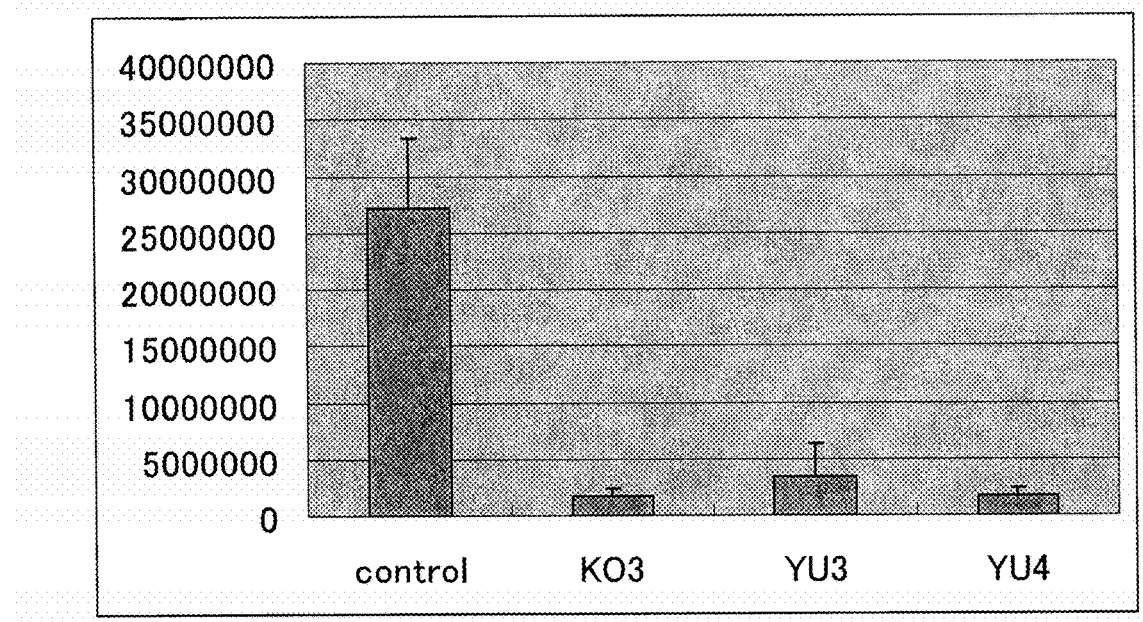
FIG. 5 is a graph showing the biofilm formation-inhibiting effect against Candida albicans.

The results are shown in FIG. 5.

The strains YU3, YU4 and KO3 strongly suppressed the biofilm formation of *Candida albicans*.

Example 1 Production of Fermented Milk (1)

*Lactobacillus rhamnosus* strain KO3 (NITE BP-771) was cultured in an MRS medium at 37° C. for 18 hours to give a preculture liquid. The liquid was washed twice with MQ water and centrifuged to collect the bacteria. The above-mentioned bacteria of the strain KO3 that had been washed, and lactose in an amount to be 0.1 to 10% against 100 mL of a milk were added to a commercially available milk to which "Danone Yogurt" (Danone Japan Co., Ltd.; bifidobacteria are used) had been added, and cultured at 37° C. for 24 hours to give a fermented milk.

Meanwhile, it is considered that, in the case when a small amount of "Danone Yogurt" (bifidobacteria are used) is added and general culturing is conducted, only a starter used in the yogurt proliferates since bifidobacteria are obligatory anaerobes.

Test Example 3 Evaluation of Fermented Milk (1)

Figure 6:
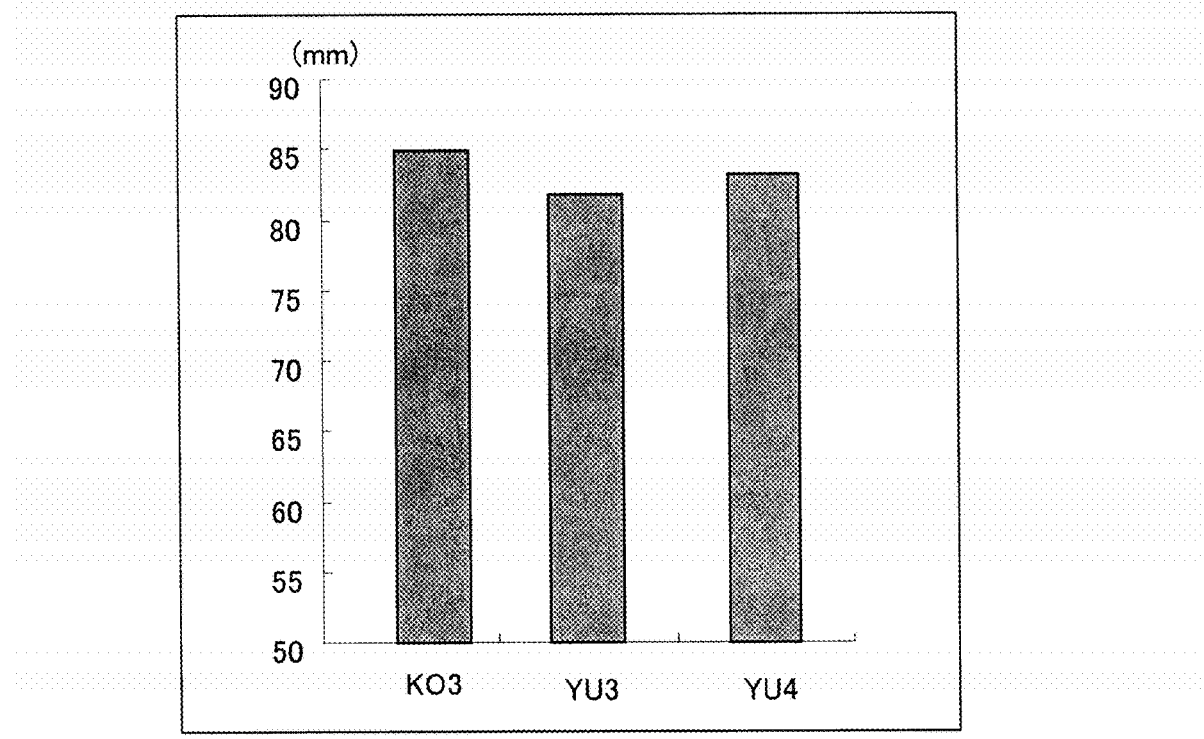
FIG. 6 is a graph showing the result of the evaluation on taste (Visual Analogue Scale (VAS) method).

A questionnaire about taste was conducted on 127 subjects by a Visual Analogue Scale (VAS) method. Each subject ate a yogurt and thereafter filled in a scale bar which comprised a line of 10 cm on which "very delicious" was described on the left end, "very distasteful" was described on the right end, and "normal" was described on the center, and the results were quantified by measuring the distances from the left end and obtaining the average value thereof. The results are shown in FIG. 6.

Furthermore, in the summary of the free opinions that were written at the same time, the subjects who wrote "tasty" or "mild" accounted for 72% in total, and thus it was confirmed that all of the fermented milks of the present invention had good taste.

Example 2 Production of Fermented Milk (2)

Raw materials containing a milk are mixed homogeneously, heated and sterilized. This was cooled, and fermented by using *S. thermophilus* as a starter and using *L. bulgaricus* and *L. rhamnosus* strain KO3 at from 37 to 40° C. to produce a yogurt (L8020). Furthermore, a placebo yogurt was produced by only *L. bulgaricus* using *S. thermophilus* as a starter.

Test Example 4 Evaluation of Fermented Milk (2)

Using the L8020 yogurt prepared in Example 2, antibacterial tests against cariogenic bacteria were conducted.

*S. mutans* ingbritt strain and *S. sobirinus* strain B13 as mentioned above were used as the cariogenic bacteria. Each strain was precultured in TSBY, and thereafter washed three times with sterilized distilled water to adjust to $1\times10^8$ cfu/ml. 1.5 mL of TSBY was dispensed into a 24-well plate, and 100 µL of the bacterial liquid was inoculated into each well.

The inside of the intercell containing each yogurt was put into a 24-well plate, and the amounts of the bacteria after 24 hours of culturing were compared.

The measurement was conducted by using the amount of the bacteria after 24 hours as the amount of ATP. Four same samples were made for each, and an average value±SD was obtained. The results are shown in FIGS. 7A and 7B.

Figure 7A:
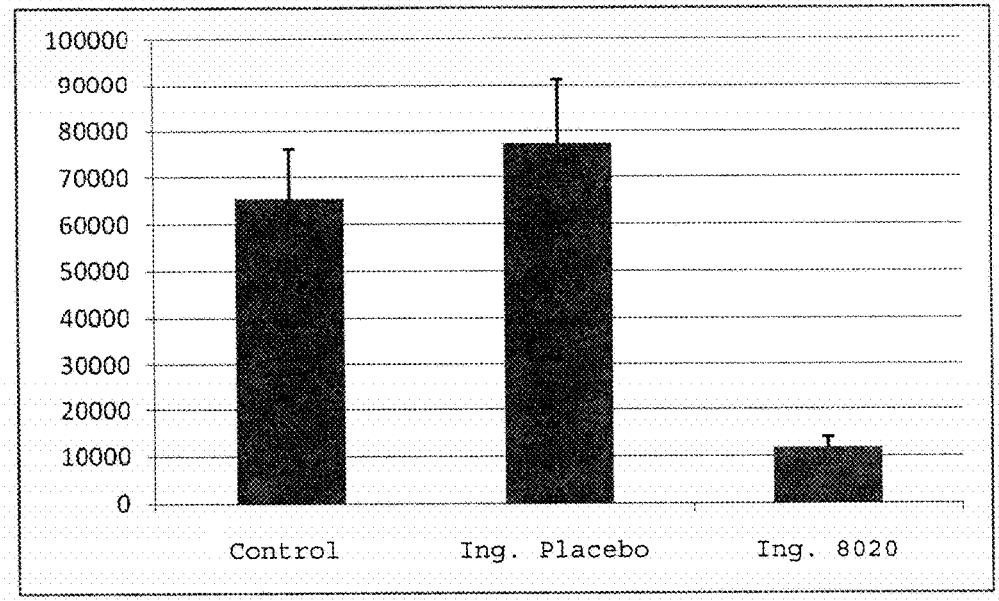
FIG. 7A is a graph showing the antibacterial action of yogurt (S. mutans ingbritt strain).
Figure 7B:
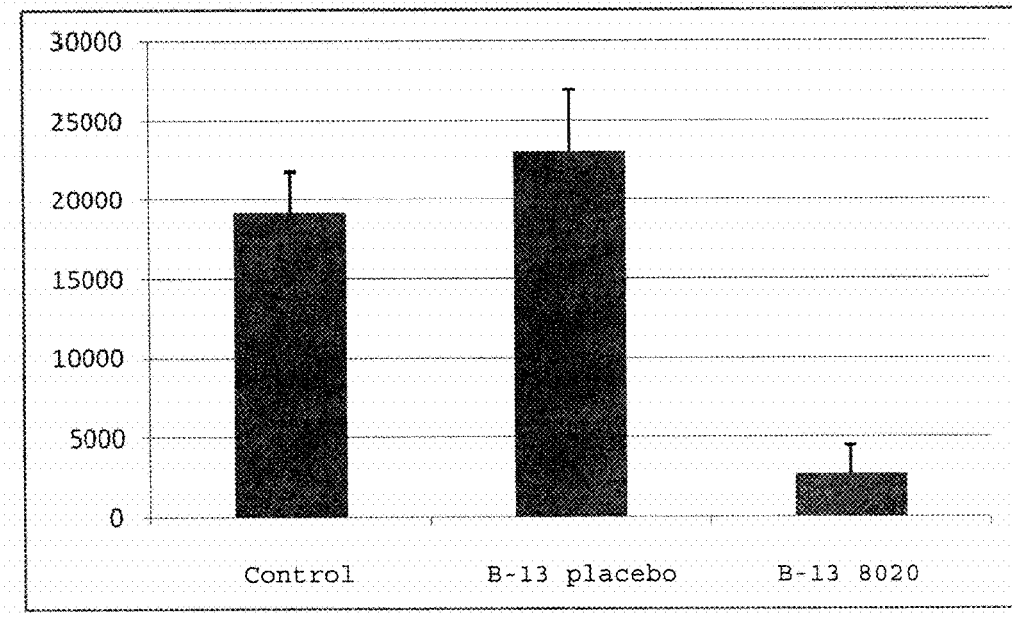
FIG. 7B is a graph showing the antibacterial action of yogurt (S. sobirinus strain B13).

In FIGS. 7A and 7B, the amount of ATP (pmol/well) is shown in the longitudinal axis of the graph; a tendency of slight increase was recognized in placebo against both the Ingbritt strain and strain B-13, whereas a significant suppression effect was also recognized in the state of the L8020 yogurt to which KO3 had been added.

Test Example 5 Evaluation of Fermented Milk (3)

Human tests were conducted by using the L8020 yogurt prepared in Example 2.

Forty subjects from 19 to 25 years of age were divided into two groups according to a random number table. The subjects in Group 1 continued to eat the placebo yogurt and the subjects in Group 2 continued to eat the L8020 yogurt, once a day at lunchtime for 2 weeks.

The carriage numbers of the cariogenic bacteria and periodontal disease bacteria in the oral cavity were calculated by collecting saliva by using a kit of BML and quantifying the cariogenic bacteria by a culture method or the periodontal disease bacteria by using a PCR-invader method or invader method for 4 kinds of bacteria: *P. intermedia* (Pi), *T. forsythensis* (Tf) and *F. nucleatum* (Fuso).

The collection of saliva was conducted at 3 days before initiation of tasting by collecting saliva on ice after stimulation for 5 minutes by a gum chewing method, and the number of carriage in the oral cavity for each of the above-mentioned bacteria was calculated and used as the pre-value of the above-mentioned tests.

After the tasting for 2-weeks, about 5 mL of stimulated saliva was collected on ice in a similar manner by a gum chewing method, and the number of carriage in the oral cavity for each of the above-mentioned bacteria was calculated and the effect in the above-mentioned test was evaluated. The results are shown in FIGS. 8A-8D.

Figure 8A:
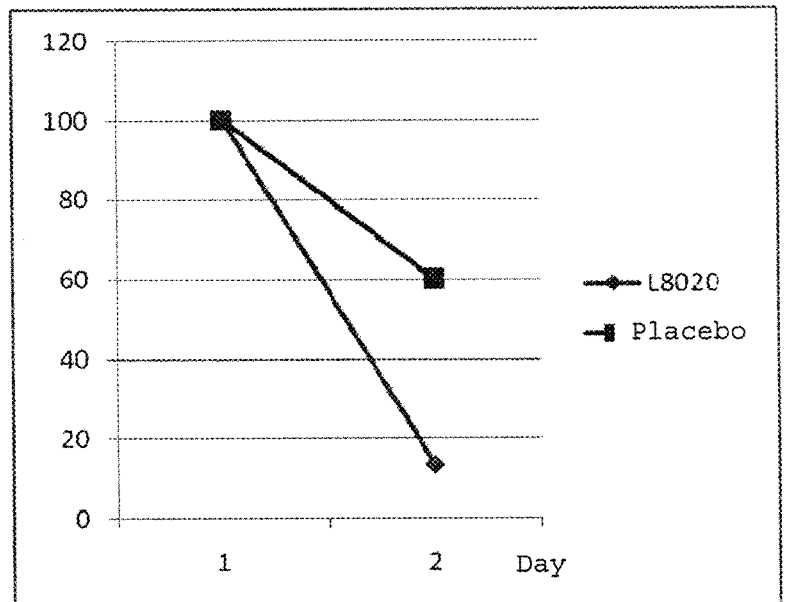
FIGS. 8A and 8B are graphs showing the effect of decreasing the numbers of cariogenic bacteria and periodontal disease bacteria in the human oral cavity.

As is apparent from FIG. 8A, when the pre-value of the number of carriage in the oral cavity of the cariogenic bacterium was defined as 100, the value was decreased to about 60% by the placebo yogurt. On the other hand, significant decrease to about 15% was observed in the L8020 yogurt. It was clarified from this result that the carriage of the cariogenic bacterium in the oral cavity is decreased significantly and effectively by ingesting the L8020 yogurt for 2 weeks.

Figure 8B:
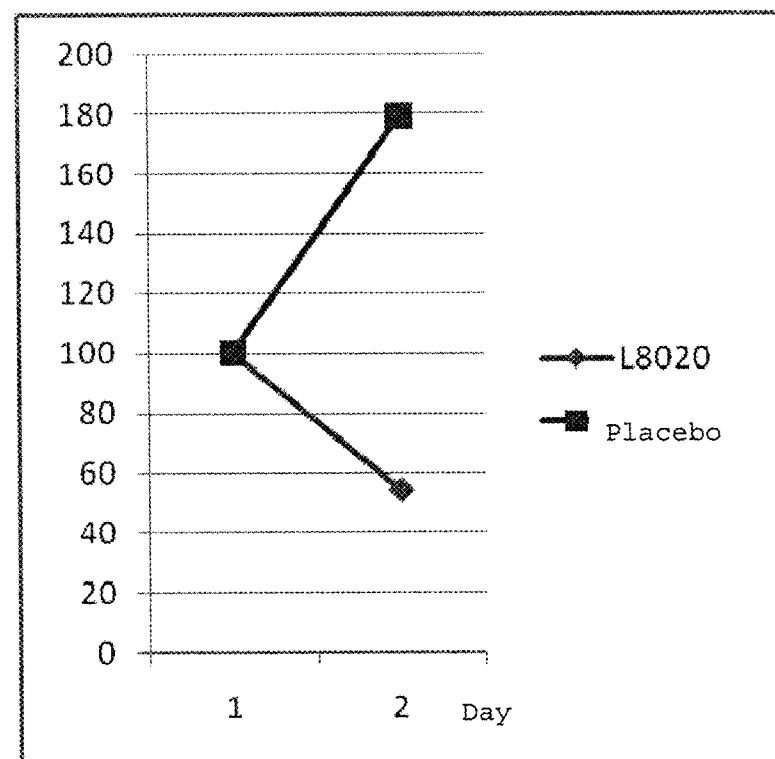

As is apparent from FIG. 8B, when the pre-value of the number of carriage in the oral cavity of the Pi bacterium was defined as 100, the value was increased to about 180% by the placebo yogurt. On the other hand, significant decrease to about 50% was observed in the L8020 yogurt. It was clarified from this result that the carriage of the Pi bacterium in the oral cavity is decreased significantly and effectively by ingesting the L8020 yogurt for 2 weeks.

Figure 8C:
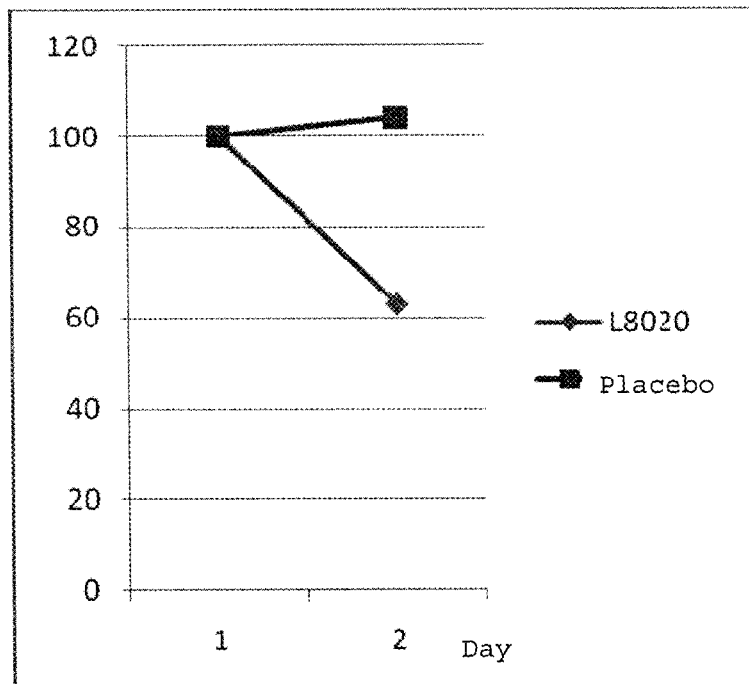
FIGS. 8C and 8D are graphs showing the effect of decreasing the numbers of cariogenic bacteria and periodontal disease bacteria in the human oral cavity.

As is apparent from FIG. 8C, when the pre-value of the number of carriage in the oral cavity of the Tf bacterium was defined as 100, the value was increased to about 105% by the placebo yogurt. On the other hand, significant decrease to about 60% was observed in the L8020 yogurt. It was clarified from this result that the carriage of the Tf bacterium in the oral cavity is decreased significantly and effectively by ingesting the L8020 yogurt for 2 weeks.

Figure 8D:
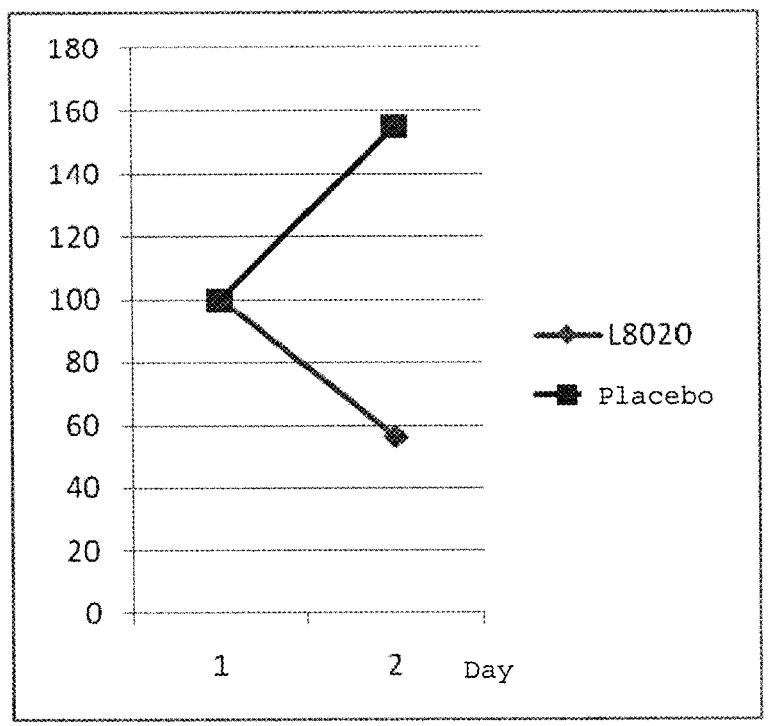

As is apparent from FIG. 8D, when the pre-value of the number of carriage in the oral cavity of the Fuso bacterium was defined as 100, the value was increased to about 160% by the placebo yogurt. On the other hand, significant decrease to about 60% was observed in the L8020 yogurt. It was clarified from this result that the carriage of the Tf bacterium in the oral cavity is decreased significantly and effectively by ingesting the L8020 yogurt for 2 weeks.

For the Pg bacterium, since the number of the carrier was small, a significant change was not observed.

It was clarified by the above-mentioned results that the L8020 yogurt significantly decreases Pi bacterium, Tf bacterium, and *Fusobacterium* bacterium that is known as a subgingival plaque former, among cariogenic bacteria and periodontal disease bacteria, and thus has a very high effect against bacteria relating to dental caries and periodontal diseases as compared to a general yogurt.

The invention claimed is:

1. A method for suppression of proliferation of a cariogenic bacterium, a periodontal disease bacterium and a *Candida* yeast in a subject in need thereof, comprising
    orally administering to the subject a composition comprising an effective amount of *Lactobacillus rhamnosus* strain KO3 (NITE BP-771) to suppress proliferation of a cariogenic bacterium, a periodontal disease bacterium and a *Candida* yeast in the subject.

2. The method according to claim 1, wherein the cariogenic bacterium, periodontal disease bacterium and *Candida* yeast are selected from the group consisting of *Streptococcus matins, Streptococcus sobrinus, Porphyromonas gingivalis*, and *Candida albicans*.

3. The method according to claim 1, wherein the composition is a food composition.

4. The method according to claim 3, wherein the food composition is a fermented milk or a fermented beverage.

5. The method according to claim 1, wherein the strain is present in the composition in an amount of 1% to 50% by mass of the composition.

6. The method according to claim 1, wherein the strain is present in the composition in an amount of 10 to 20% by mass of the composition.

7. The method according to claim 1, wherein the composition is a liquid and comprises the strain in an amount of $1 \times 10^6$ cells/ml to $1 \times 10^8$ cells/ml.

8. The method according to claim 1, wherein the composition is a liquid and comprises the strain in an amount of $1 \times 10^7$ cells/ml to $1 \times 10^{10}$ cells/ml.

9. The method according to claim 1, wherein the subject is a human and the method comprises administering a composition comprising viable *Lactobacillus rhamnosus* strain KO3 (NITE BP-771), in an amount from $1 \times 10^8$ to $5 \times 10^{10}$ cfu/day.

10. The method according to claim 1, wherein the administering comprises ingesting.

* * * * *